United States Patent
Harrisson, III

[11] Patent Number: 5,833,458
[45] Date of Patent: Nov. 10, 1998

[54] GRADUATED ENDODONTAL SWAB

[76] Inventor: Louie V. Harrisson, III, 14 Rolling Green Cir., Winona, Miss. 38967

[21] Appl. No.: 736,340

[22] Filed: Oct. 23, 1996

[51] Int. Cl.[6] .................................................... A61C 5/01
[52] U.S. Cl. ........................................... 433/102; 433/224
[58] Field of Search ................................ 433/72, 81, 102, 433/224

[56] References Cited

U.S. PATENT DOCUMENTS

| | | | |
|---|---|---|---|
| 2,846,927 | 8/1958 | Masci et al. | 132/321 |
| 2,927,056 | 3/1960 | Gurney | 433/224 |
| 4,212,639 | 7/1980 | Schaffner | 433/72 |
| 4,273,531 | 6/1981 | Hasegawa | 433/27 |
| 4,364,730 | 12/1982 | Axelsson | 433/72 |
| 4,457,710 | 7/1984 | McSpadden | 433/81 |
| 4,462,802 | 7/1984 | Sekiya | 433/72 |
| 4,501,555 | 2/1985 | Ditchburn | 433/29 |
| 4,565,722 | 1/1986 | Highgate et al. | 433/224 |
| 5,000,683 | 3/1991 | Brock | 433/72 |
| 5,016,659 | 5/1991 | Mas | 132/329 |
| 5,104,322 | 4/1992 | You | 433/224 |
| 5,423,677 | 6/1995 | Brattesani | 433/72 |

*Primary Examiner*—Nicholas D. Lucchesi
*Attorney, Agent, or Firm*—Pravel, Hewitt & Kimball

[57] ABSTRACT

An absorbent dental point is provided with a scale of graduated depth indicators, arranged in a manner such that the depth to which the tip of the dental point has been inserted into a root canal may be quickly and reliably measured each and every time a subsequent dental point is inserted in the root canal in the course of a root canal procedure.

7 Claims, 2 Drawing Sheets

GRADUATED ENDODONTAL SWAB

BACKGROUND OF THE INVENTION

This invention relates to endodontal surgery and particularly to instruments employed therein including absorbent pointed probes utilized as swabs in such as root canal surgery.

While becoming less common in the developed countries through better education of the public in the care of the mouth, the inclusion of antidecay additives to such as the water supply and improvements in dental cleaners and washes, decay of the teeth still remains a common problem. When decay of a tooth is quickly noted and has penetrated the enamel (the outer hard surface of the tooth) and only nominally into the dentin (the calcareous portion as opposed to the pulp and nerve structure) repair is readily made by the treatment of cleaning out the affected tissue of the tooth, replacing it with a synthetic material (such as a dental amalgam). Thus, the tooth is said to have been filled, as by the cavity (formed by the removal of the decayed, diseased dentine) being replaced by the filling material.

If the progress of the decay of the tooth (caries) is allowed to progress into the next inner layer, i.e., the pulp containing the nerve and blood vessels, the required treatment to arrest the continuing decay is likely a "root canal", known from its inclusion in the procedure. When the decay of the tooth reaches the pulp, it likely becomes inflamed and may die. Involvement of the pulp usually results in root-end abscess and the associated infection may be passed by the blood stream to other parts of the body, producing inflammation, secondary abscess or other disease. Endodontic treatment, if initiated immediately after injury or involvement of the pulp, can prevent formation of dental abscess, or if the abscess has developed, can usually eliminate the infection without extraction of the tooth. Removal of the pulp includes removal of the live tissue including the nerves and capillary vessels of the tooth. This procedure includes the cleaning of the hollow, canal-like portions of the tooth extending into the tooth's root, by which it is anchored into the jaw bone. Once the tooth, including the root canal, is completely cleaned, the hollow is filled with an air-tight sealer (commonly including medicaments to destroy microorganisms and promote healing) and the remaining cavity filled with the amalgam, or similar material.

The process of adequately cleaning the root canal is a demanding one, requiring the absolute cleaning and sterilization of the canal, otherwise, a "dead cavity" may result. The "dead cavity" is one in which there is remaining tissue to decompose and cause further disease or abscess and may allow further decay within and adjacent the affected tooth including the surrounding periodontal tissue and occasioning the loss of supporting bone and, ultimately, the tooth. The meticulous process of the "root canal" begins with the removal of the diseased, decayed dentine by drilling and aspiration of that tissue and the underlying pulp. The capillaries and nerves contained in the interstices of the canals within the root are first loosened and scraped with narrow files. The canals are then cleaned and dried with absorbent dental points, the subject of the present invention.

As explained above, the adequate cleaning of the root canal requires the dentist to probe, scrape, clean and dry the full extent of the interstices of the canal. Subsequent to the cleaning and drying, a medicament is then applied, taking care that it too, reaches the full extent of the canal. Disease of the tooth, once penetrating the dentine into the pulp, allows one or more of a variety of microorganisms and bacteria to quickly infiltrate the far reaches of the canal. The same type of absorbent dental point may be utilized to deliver the medicament to the extent of the canal as was used to dry it, being typically dipped into the medicament and then routed down into the canal.

It is imperative that the treatment of the root canal is conducted to achieve the highest degree of asepsis as is possible. It is common for the dentist to utilize a dozen or more absorbent points during a procedure. On each occasion, the dentist must gauge the depth of the tip of point into the canal to ensure adequate cleaning, drying and medication to the particular depth desired. Commonly, the dentist has measured the depth of the canal (including branches and turns therein), or the several canals in the case of molars, with prior specialized instruments utilized in the drilling, scraping and filing process. Thus, it is important for the dentist to be reassured that the absorbent points are repeatedly inserted to the particular measured depths for selective treatment of the entire canal as the root canal procedure is conducted. Until the present invention, an absorbent dental point having the necessary measurement means has not been available to provide the assured, selective insertion of the absorbent dental point into a predetermined depth of the open root canal.

DESCRIPTION OF THE PRIOR ART

Absorbent dental points have been used by dentists for many years. Paper points, as they are commonly called, are conventionally formed of special types of paper or synthetic materials exhibiting similar properties. The conventional paper point should exhibit a wicking action so as to imbibe exudates present in the root canal or pulp cavity. As discussed above, the paper point should also be capable of absorbing medicaments such that they may be subsequently delivered to the selected location of the root canal. As may be expected, the point must be sufficiently stiff to be insertable into the small opening of the root canal, yet sufficiently flexible to follow the tortious path of the canal to its end. An additional quality of a suitable paper point is lateral and longitudinal strength to withstand the manipulation of the tip as treatment is effected on the root canal. This lateral and longitudinal strength must persist though the paper point is saturated with exudate or medicament.

U.S. Pat. No. 2,846,927 describes the manufacture of absorbent dental points of fibrous sheets of manila hemp, being tightly wound from a triangular sheet into an elongated, round shaft of slightly decreasing diameter from the held end to the operative or tip end.

Specialized paper points have been developed for the delivery of medicaments into the root canal. U.S. Pat. No. 5,104,322 is directed to root canal sealers and cleaners having color coded heads to permit easy identification of the diameter of the tip portion of the of the paper point. The patent distinguishes between absorbent dental points utilized as sealers, to which the disclosed invention is directed, from absorbent dental points utilized as cleaners (the primary use of absorbent points of the present invention). The patented invention teaches color coding of the heads of the points, ranging from 0.15 mm in diameter and 1.4 mm in diameter. The teaching recognizes that absorbent dental points are conventionally manufactured in lengths of approximately 28 to 30 mm.

Several patents are directed to graduated periodontal instruments for judging the depths of the effects of gingivitis and the resulting cavity created by bone loss in the affected gum adjacent a tooth. Most of these devices include mechanism for assuring that, on insertion of the probe into the diseased periodontal area, touch of the probe is maintained at a constant pressure as the probe is used to explore the bone loss associated with the disease. U.S. Pat. Nos. 5,423,677; 5,096,420; 5,000,683; 4,768,952; and 4,340,069 are illustrative of these specialized instruments.

SUMMARY OF THE INVENTION

The principal objective of the present invention is to provide an absorbent dental point instrument which includes a graduated depth scale on the shaft of the instrument by which a dentist may readily identify the depth of insertion of the tip of the instrument.

It is another object of the present invention to provide an absorbent dental point instrument, the tip of which may be selectively inserted to a predetermined depth to affect a desired treatment during root canal surgery.

It is a further object of the present invention to provide an absorbent dental point instrument, during the use of which, the dentist may confirm treatment to the maximum depth of the root canal.

A still further object of the present invention is the inclusion of an inventive graduated depth scale on an absorbent dental point which promotes rapid and reliable reading of the depth of the tip of such a dental point.

DETAILED DESCRIPTION OF PREFERRED EMBODIMENTS

Figure 1:
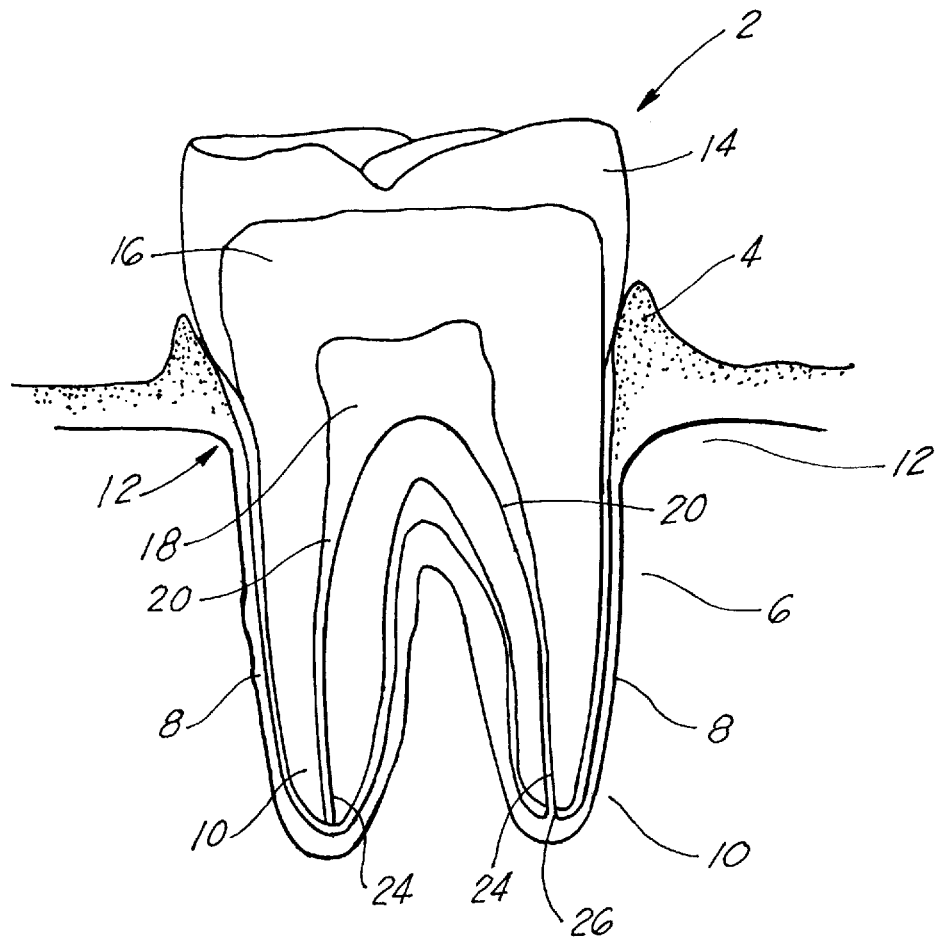
FIG. 1 is a pictorial view, partially in section, of a tooth, illustrating the tooth structure and root canal into which the present invention is inserted during use.

In order that the present invention might be better appreciated, reference is made to FIG. 1 which illustrates, in a sectional drawing, the interior of a tooth (herein a molar). Tooth 2 is anchored into gum 4 and adjacent jaw bone 6. Surrounding the tooth 2 is a periodontal membrane 8 which forms an envelope around the roots 10 of tooth 2. At the surface of the jaw bone, the periodontal membrane merges into the gum as at 12. Tooth 2 includes enamel 14, forming the hard, exterior of the tooth 2, and is composed mostly of the mineral calcium. Under enamel 14 is dentin 16 which forms the main core of tooth and it is composed generally of calcified tissue, calcium and phosphorous. The dentin 16 is highly sensitive and includes a labyrinth of tubules for the circulation of lymph.

The central structure of the tooth 2 is the nerve or, more commonly, the pulp 18. Pulp 18 is contains nerves, lymph, blood vessels and fibrous tissue. The pulp 18 is connected to the life systems through the pulp (or root) canal 20 which extends about 75% of the length of the tooth, down into the root 10 via the pulp canal 24. The pulp canal terminates in apical foramen (holes) 26 at the tip of roots 10 and through which the nerves, blood vessels and lymph join their respective systems in the body. Lining the pulp cavity is a layer of odontoblasts, whose original function was to produce the dentine and which may be activated again by such as injury or tooth decay to again begin producing a secondary, protective layer of dentin. With appreciation of the nature of the composition and extent of the pulp canal, the present invention may be better appreciated as providing an instrument which can assist the dentist in removing all of the soft tissue and contained microorganisms from the canal and dry it such that a successful sealing and immobilization of the canal may be achieved.

Figure 2:
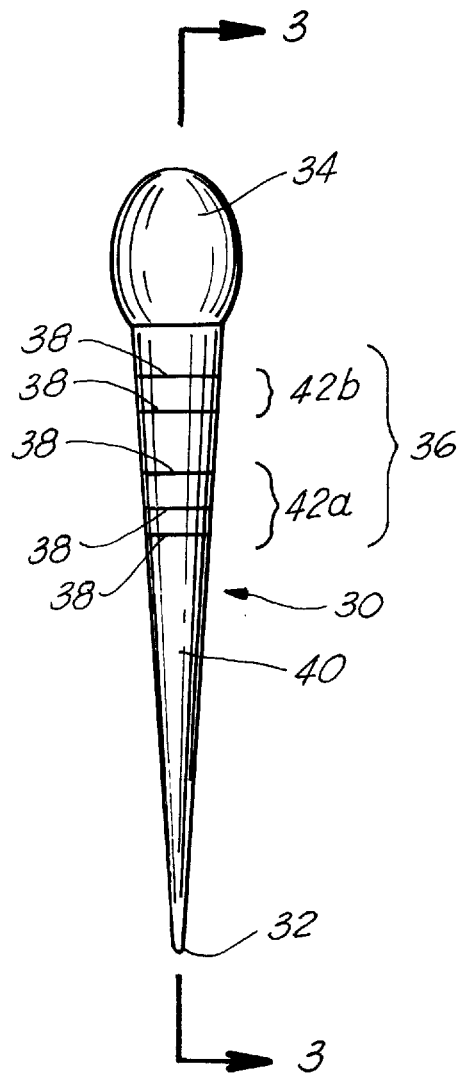
FIG. 2 is an elevational view of the absorbent dental point of the present invention.
Figure 3:
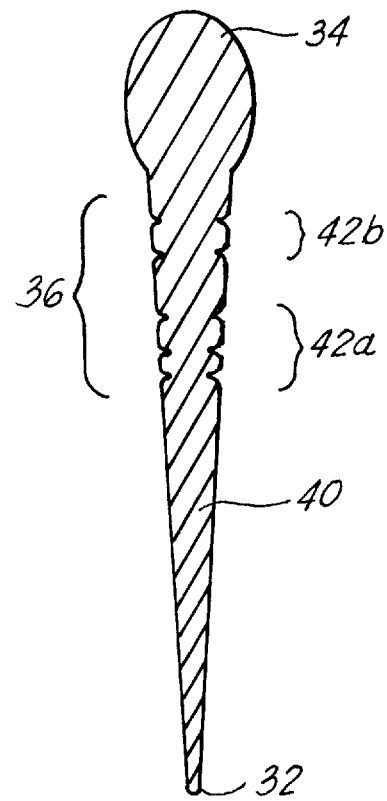
FIG. 3 is a sectional view of the embodiment of the embodiment of the present invention illustrated in FIG. 2, taken along the line 3—3 in that view.

Referring now to FIG. 2, a preferred embodiment of the present invention is illustrated. The present invention is embodied in an absorbent dental point 30 (more commonly referred to as a paper point). Absorbent dental points are conventionally 28 mm to 30 mm in length, as measured from tip 32 to head end 34, and are available from a variety of sources such as Johnson & Johnson, Caulk, Kerr and Dident. Absorbent dental point 30 according to the present invention is illustrated as including a graduated depth scale 36 having indicators 38 disposed in ascending or descending relation on shaft 40 of point 30. Indicators may be placed upon point 30 in a variety of ways, well known in the art, including marking by dyes or inks or by such as scribing an imprint or indentation (e.g., engraving) into the surface of the shaft 40.

In a preferred embodiment of the present invention, scale 36 is made up of depth indicators 38, placed on point 30 in separated groupings, 42a and 42b. In the illustrated embodiment, indicators 38 are spaced at locations indicating a depth (or operational length of point 30 below the specific indicator) of 18, 19, and 20 mm and 22 and 24 mm, as measured from tip 32. As should be appreciated, during the carrying out of a root canal procedure, the mouth cavity becomes quite congested with equipment and instruments, including the suction tube for aspirating debris and fluids from the site, a frame and rubber dam around the subject tooth to shield the rest of the mouth from by-products of the procedure and the dentists fingers and instruments as the procedure is carried out. By providing scale 36 having separate groupings (42a and 42b) of indicators 38, a determination of the depth of the tip 32 of point 30 is more readily observed.

In the embodiment wherein three indicators are placed in a grouping (at one millimeter intervals in the illustrated embodiment) as at 42a and two indicators are placed in a grouping (at a two millimeter spacing in the illustrated embodiment) as at 42b, the observation and distinguishing the depth value of a particular indicator 38 on scale 36 as determinative of the depth of tip 32 is readily accomplished. Since the depth indicators 38 of grouping 42a are at one millimeter increments, this grouping is readily differentiated from grouping 42b, in which lines are spaced in two millimeter increments. Likewise, since the numbers of depth indicators 38 within each grouping are limited to two and three indications (i.e., a different number), the distinguishing of the relevant indicator 38 on scale 36 and the accurate measurement of the depth of the canal is readily accomplished.

One skilled in the art will recognize that distinguishable groups of other combinations and values of indicators 38 are within the scope of the present invention. Since the absorbent dental point of the present invention allows the dentist to quickly and reliably measure the depth of the root canal on each and every insertion of a point 30 into the root canal, the effective cleaning, drying and coating of a canal may be reliably performed.

As will be apparent to persons skilled in the art, various additional modifications, adaptations and variations of the foregoing specifically disclosed embodiments and methods of coating removal may be made without departing form the objectives and scope of the present invention. Various modifications and changes may be made to the embodiments disclosed herein by those skilled in the art and such are contemplated by the present invention and are to be understood as included within the spirit and scope of the appended claims.

What is claimed is:

1. An absorbent dental point for cleaning a root canal comprising:
    a) a shaft portion terminating at its respective ends in a tip portion and a head portion;
    b) said shaft portion have a cross section of decreasing diameter from said head portion to said tip portion;
    c) a readily discernable depth scale disposed on said shaft disposed generally adjacent said head portion of said shaft, said scale having a plurality of indicators inscribed on said shaft each said indicator designating a predetermined distance on said shaft with respect to said tip;
    d) wherein said scale includes a group of a plurality of indicators, wherein each of said indicators are disposed in uniform increments successively with respect to said tip;
    e) wherein said scale includes a second group of a plurality of indicators, wherein each of said second group of indicators are disposed in uniform increments successively with respect to said tip; and
    f) wherein said indicators in said second group are spaced in increments at least twice the spacing of said indicators of said first group.

2. An absorbent dental point in accordance with claim 1 wherein each said indicator is a line on said shaft, substantially perpendicular to the axis of said shaft.

3. An absorbent dental point in accordance with claim 2 wherein said line is disposed circumferentially around said shaft.

4. An absorbent dental point in accordance with claim 2 wherein said line is printed on said shaft.

5. An absorbent dental point in accordance with claim 2 wherein said line is engraved on said shaft.

6. An absorbent dental point in accordance with claim 1 wherein said first group of indicators include three indicators spaced at 18, 19 and 20 millimeters respectively from said tip of said shaft.

7. An absorbent dental point in accordance with claim 1 wherein said second group of indicators include two indicators spaced at 22 and 24 millimeters, respectively from said tip of said shaft.

* * * * *